United States Patent [19]

Gambert et al.

[11] Patent Number: 4,894,138
[45] Date of Patent: Jan. 16, 1990

[54] ELECTROCHEMICAL GASEOUS MEASUREMENT CELL

[75] Inventors: Rudolf Gambert, Arfrade; Uwe Kuehn, Lubeck, both of Fed. Rep. of Germany

[73] Assignee: Drägerwerk AG, Lübeck, Fed. Rep. of Germany

[21] Appl. No.: 235,385

[22] Filed: Aug. 22, 1988

[30] Foreign Application Priority Data

Sep. 2, 1987 [DE] Fed. Rep. of Germany ....... 3729287

[51] Int. Cl.⁴ ............................................ G01N 27/46
[52] U.S. Cl. .................................................... 204/415
[58] Field of Search ................. 204/415, 431; 128/635

[56] References Cited

U.S. PATENT DOCUMENTS

| | | | |
|---|---|---|---|
| 2,411,674 | 11/1946 | Wilson | 204/52.1 |
| 3,835,013 | 9/1974 | Grubb et al. | 204/415 |
| 4,495,051 | 1/1985 | Fujita et al. | 204/408 |
| 4,789,453 | 12/1988 | Eberhard et al. | 204/412 |

FOREIGN PATENT DOCUMENTS 17144 1/1984 Japan ................................. 204/415

OTHER PUBLICATIONS

J. K. Dennis et al., "Nickel and Chromium Plating", pp. 119 & 120, (1972).

Primary Examiner—G. L. Kaplan
Attorney, Agent, or Firm—McGlew & Tuttle

[57] ABSTRACT

An electrochemical gaseous measurement cell includes a housing with an anode and a cathode arranged in spaced locations in an acid electrolyte for galvanic measurement of gases which comprises an aqueous solution of an organic acid containing a polyfunctional groups suitable to yield protons during the measurement. The container, or housing, also has a membrane at an opening thereof which is permeable to oxygen.

10 Claims, 1 Drawing Sheet

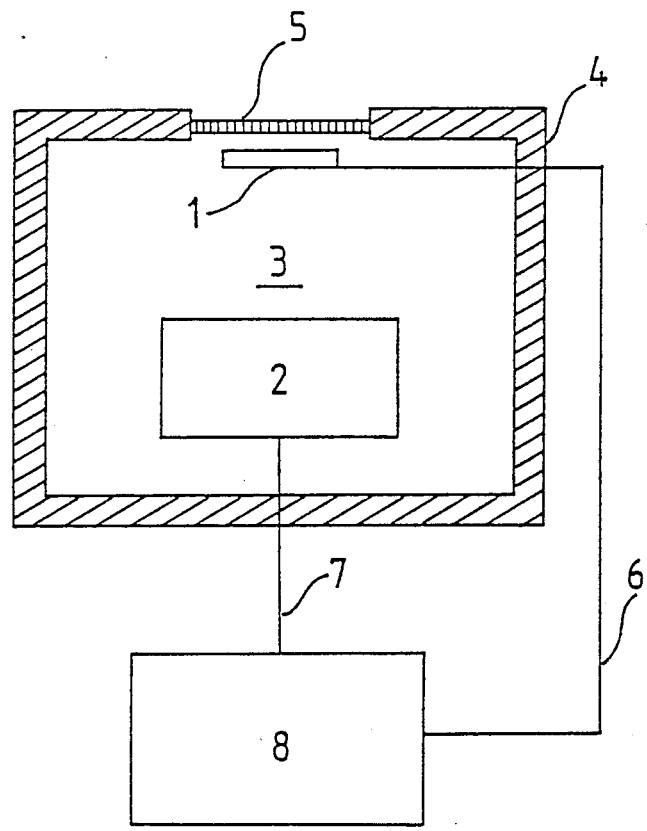

ELECTROCHEMICAL GASEOUS MEASUREMENT CELL

BACKGROUND OF THE INVENTION

1. Field of the Invention

This invention relates in general to gaseous measurement devices and in particular to a new and useful electrochemical measurement cell for measuring gases.

The invention concerns an electrochemical measurement cell with an anode and a cathode, which are placed in an acid electrolyte for galvanic measurement of oxidizable gases, especially oxygen, and accommodated in a housing, which closes off the electrolyte volume against the gas atmosphere to be investigated by means of a permeable membrane.

Such measurement cells are used preferably to detect oxygen in air, whereupon the oxygen diffusing through the membrane into the electrolyte is reduced. At the cathode, oxygen is reduced to water, protons being consumed and electrons given off. The protons necessary for this must be provided by the electrolyte.

As acid electrolytes, one employs monocarboxylic acids such as acetic acid, propionic acid, or butyric acid in aqueous solution. The degree of dissociation of these acids is so slight, however, that the conductivity needed for an oxygen measurement cannot be achieved unless salts of these acids are added.

A similar electrochemical measurement cell with an acid electrolyte is described in U.S. Pat. No. 4,495,051.

In the known electrochemical measurement cell, protons are continuously consumed during the measurement, which must be taken from the electrolyte. This proton capacity is quickly depleted in the case of the monocarboxylic acids which are used. When the proton reserve is exhausted, no further operation of the measurement cell is possible, so that its lifetime is very restricted. The continuing proton consumption produces a shifting of the pH value of the electrolyte solution in the alkaline direction. If this value exceeds pH 7, poorly soluble bicarbonates and ultimately carbonates may be formed, which impair the functioning of the measurement cell. A passivation layer is then formed on the anode and a carbonate layer between the cathode and the diffusion membrane, resulting in a larger overvoltage and, thus, lower conductivity.

Addition of salts of the particular acids, such as alkaline metal and/or ammonium salts, although increasing the conductivity by virtue of their high degree of dissociation, does not produce a larger proton capacity of the electrolyte. Furthermore, there is a limit to the quantity of salts that can be added, since these increase the pH of the solution by virtue of their basic nature, which has an undesirable effect on the $CO_2$ stability of the sensor, especially if the pH limit of 7 is exceeded. In many applications, especially during measurement of oxygen in respiration gas, a large proportion of $CO_2$ in the investigated gas is to be expected. Since the membrane closing off the electrolyte from the surrounding gas atmosphere may be permeable to $CO_2$, the contact between the electrolyte and the $CO_2$ present in the air of the environment results in further formation of carbones and bicarbonates. This is manifested by a shifting of the pH to lower values, resulting in a deposition of lead oxide and lead carbonate on the anode surface in the case of lead anodes. Since the poor solubility of lead carbonates may result in precipitation of salts, the function of the cathode is impaired, as additional diffusion barriers are presented to the diffusing oxygen. Furthermore, the formation of crystals exerts a mechanical pressure on the diffusion membrane, producing a stress on the thin diffusion membrane.

Because of the large vapor pressure of the acid electrolytes employed thus far, a not insignificant diffusion of the electrolyte occurs through the membrane, and also through the walls of the housing, inasmuch as the walls consist almost always of plastic in recent time.

All these undesirable features are aggravated even further when a miniaturization of the outside dimensions of the measurement cell is desired. In such case, there is an unfavorable shifting in the ratio of the surface of the electrodes and inner housing to the volume of the electrolyte, whereupon the surface-related perturbations, such as diffusion from the membrane, passivation of the anode surface, increase in the electrolyte resistance, are intensified.

SUMMARY OF THE INVENTION

The present invention, accordingly, provides an improved electrochemical measurement cell in such a way that the proton capacity of the electrolyte is increased without further admixtures and the electrolyte resistance is lowered, in order to achieve a better linearity of the measurement signal and a longer lifetime of the entire measurement cell.

According to the invention an aqueous solution of an organic acid as the electrolyte is used which contains polyfunctional groups suitable for surrender of protons during the measurement.

These organic acids have the advantage of being able to yield several protons per molecule, under the identical molar concentrations as the customary acids. Apart from this higher proton capacity, this electrolyte has better conductivity, so that the process may occur without addition of conductivity-boosting salts and the consequent raising of the pH value.

Compared to the customary acid electrolytes, the polyfunctional acids typically exhibit a lifetime that is longer by a factor of 3 and a conductivity that is higher by a factor of 5, other conditions remaining equal.

With increasing number of polyfunctional groups within the acid, the vapor pressure is lowered and the permeation capacity is reduced, so that loss of electrolyte liquid as a result of permeation through the membrane or diffusion through the walls of the plastic housing are equally discouraged.

It has proven especially advantageous to select an aliphatic or aromatic di-/tricarboxylic acid or di-/trisulfonic acid as the acid containing polyfunctional groups.

The especially favorable qualities of these compounds is in their electrochemical behavior with respect to the low background currents arising in the electrolyte when the measurement cell is flushed with inert gas, such as nitrogen, for calibration purposes. The response of the measurement cell to oxygen is prompt, and the activity of the lead or cadmium anodes is not impaired by, say, formation of a thick layer on the anode surface, since the salts of the mentioned acids are readily soluble in the electrolyte.

Suitable aliphatic or aromatic acids advantageously include, e.g., methane sulfonic acid, benzene di-/trisulfonic acid, or phenol di-/trisulfonic acid. But it may also be more expedient to use phthalic acid. A particularly suitable alphatic carboxylic acid is citric acid. This presents no problems in its processing, it is neutral in smell and physiologically unobjectionable, which is particularly significant when using the measurement cell in the respiration gas circulation of a medical instrument. Furthermore, it is distinguished by a low vapor pressure, which is negligible compared to the vapor pressure of 20.8 mm Hg for acetic acid at 30 degrees C., so that permeation and diffusion effects may be disregarded.

The especially high dissociation of the polyfunctional acids results in a desirable high conductivity, but in the event of rather high acid concentrations this produces a pH value so low that the release of hydrogen at the anode may prove inconvenient. Relatively base metals such as lead and cadmium, specifically, may pass into solution in aqueous and especially in increasingly acid environment, decomposing water and liberating hydrogen. This process is undesirable, as it consumes the anode material. It has been found that no impairment of the measurement cell functioning from hydrogen liberation can be detected down to a pH value of 3, in the case of lead or cadmium anodes. In order to avoid instances where this pH is passed, it is advisable to add a zwitterion buffer to the electrolyte, whereby the pH range can be adjusted between 3 and 7. There are several requirements for this buffer: it should exhibit good buffering capability in the indicated pH range, while being devoid of electrochemical activity and especially exhibiting no redox properties. When using lead anodes, it must be compatible with lead ions. These requirements are satisfied in especially suitable manner by zwitterion buffers of the morpholino-, amino-, and iminodiacetic or sulfonic acid type.

To assess the lifetime of measurement cells with an electrolyte with polyfunctinal proton-yielding groups under given electrolyte volume, concentration, and oxygen consumption, it has been found that, in the case of acetic acid or other monocarboxylic acids with a mean current flux of around 10 mA, and electrolyte volume of 1 mL, and an electrolyte concentration of 3 N, approximately one year passes before a pH value of 6.8 is reached, whereas a lifetime of around 3 years can be achieved with a citric acid electrolyte. This lifetime can be further raised by a factor of 1.5–2 through addition of zwitterion buffers representing additional proton sources. A miniaturized measurement cell with a polyfunctional acid electrolyte can be reduced to 1/5 the size of a measurement cell with an aqueous alkaline electrolyte.

Accordingly, it is an object of the invention to provide an inproved electrochemical measurement cell for gases which comprises a housing having an opening with a porous membrane enclosing the opening which is permeable to oxygen and containing an acid electrolyte therein which comprises an aqueous solution of an organic acid containing a polyfunctional group suitable to yield protons during the measurement and including a permeable membrane which closes off the electrolyte volume against the gas atmosphere being investigated and further includes a cathode and an anode arranged in spaced relationship and connected to an evaluation unit. A further object of the invention is to provide a device for testing particular gases in the atmosphere which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiment of the invention is illustrated.

BRIEF DESCRIPTION OF THE DRAWINGS

In the drawings:

The only figure of the drawings is a schematic sectional view of an electrochemical measurement cell constructed in accordance with the invention.

DESCRIPTION OF THE PREFERRED EMBODIMENT

Referring to the drawings in particular the invention embodied therein comprises a container or housing 4 having an electrolyte 3 therein which is closed off from the gas to be detected by a permeable membrane 5 which is permeable at least to oxygen.

The single drawing shows an electrochemical measurement cell with a cathode 1 and an anode 2, which are placed in an electrolyte volume 3 of the measurement cell housing 4. The electrolyte volume 3 is filled with an aqueous solution of citric acid. The electrolyte volume 3 is closed off against the environment by a membrane 5 permeable to oxygen. The cathode 1 and the anode 2 have measurement leads 6 and 7 which are led out through the housing 4 and conected to an evaluation unit 8 for further processing of the measurement signal.

An electrochemical measurement cell with an anode and a cathode, which are placed in an acid electrolyte for galvanic measurement of gases, particularly reducible gases such as oxygen, and accommodated in a housing, is to be improved such that its proton capacity is increased, without further admixtures to the electrolyte, and its electrolyte resistance is lowered. Improved linearity of the measurement signal and a longer lifetime of the overall measurement cell should be achieved. For this, an aqueous soltution of an organic acid possessing polyfunctional groups that are capable of yielding several protons during the meassurement is chosen as the electrolyte.

While a specific embodiment of the invention has been shown and described in detail to illustrate the application of the principals of the invention, it will be understood that the invention may be embodied otherwise without departing from such principles.

What is claimed is:

1. An electrochemical measurement cell, comprising a housing, an acid electrolyte for galvanic measurement of gases comprising an aqueous solution of an organic acid containing polyfunctional groups suitable to yield protons during measurement, an anode and a cathode arranged in said electrolyte in spaced relationship, a gas evaluation unit connected between said anode and cathode for measuring the gas, and a permeable membrane closing off said electrolyte against the surrounding atmosphere being investigated.

2. An electrochemical cell according to claim 1, wherein said organic acid containing polyfunctional groups comprises an aromatic or aliphatic di- or tri-carboxylic acid or an aromatic or aliphatic di- or tri-sulfonic acid.

3. An electromechanical measurement cell according to claim 2, wherein said organic acid is a citric acid.

4. An electrochemical measurement cell comprising: a housing; an anode positioned within said housing; a cathode positioned within said housing said housing including an opening; an acid electrolyte for galvanic measurement of gases such as oxygen, said electrolyte positioned within said housing and being formed of an aqueous solution of an organic acid containing polyfunctional groups suitable to yield protons during measurement; and a permeable membrane extending across said opening for separating said electrolyte from a gas atmosphere being investigated.

5. An electrochemical measurement cell according to claim 4, wherein said organic acid containing polyfunctional groups comprises an aromatic or aliphatic di- or tri-carboxylic acid or an aromatic or aliphatic di- or tri-sulfonic acid.

6. An electrochemical measurement cell according to claim 5, wherein the acid is citric acid.

7. An electrochemical measurement cell according to claim 4, wherein said electrolyte includes a zwitterion buffer.

8. An electrochemical measurement cell according to claim 7, wherein said buffer is an aminodiacetic or sulfonic acid.

9. An electrochemical measurement cell, comprising a housing, an acid electrolyte for galvanic measurement of gases comprising an aqueous solution of an organic acid containing polyfunctional groups suitable to yield protons during measurement, an anode and a cathode arranged in said electrolyte in spaced relationship, a gas evaluation unit connected between said anode and cathode for measuring the gas, a permeable membrane closing off said electrolyte against the surrounding atmosphere being investigated and a zwitterion buffer added to said electrolyte.

10. An electrochemical measurement cell according to claim 9 wherein said buffer comprises an iminodiacetic acid and a sulfonic acid.

* * * * *